(12) United States Patent
Govari

(10) Patent No.: US 7,729,742 B2
(45) Date of Patent: Jun. 1, 2010

(54) WIRELESS POSITION SENSOR

(75) Inventor: Assaf Govari, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 1383 days.

(21) Appl. No.: 10/029,473

(22) Filed: Dec. 21, 2001

(65) Prior Publication Data

US 2003/0120150 A1    Jun. 26, 2003

(51) Int. Cl.
*A61B 5/05*    (2006.01)

(52) U.S. Cl. ............... 600/424; 600/407; 600/425; 600/427; 600/410; 600/411; 600/109; 600/133; 600/160; 600/169; 600/176

(58) Field of Classification Search ............... 600/424, 600/407, 425, 427, 410, 411, 414, 417, 109, 600/133, 160, 169, 176; 128/898, 899; 324/207.11–207.22; 701/213, 214, 215, 216
See application file for complete search history.

(56) References Cited

U.S. PATENT DOCUMENTS

| | | | |
|---|---|---|---|
| 4,173,228 A | 11/1979 | Van Steenwyk et al. | |
| 4,905,698 A | 3/1990 | Strohl, Jr. et al. | |
| 5,057,095 A * | 10/1991 | Fabian | 604/362 |
| 5,099,845 A | 3/1992 | Besz et al. | |
| 5,391,199 A | 2/1995 | Ben-Haim | |
| 5,425,367 A | 6/1995 | Shapiro et al. | |
| 5,425,382 A | 6/1995 | Golden et al. | |
| 5,443,489 A | 8/1995 | Ben-Haim | |
| 5,558,091 A | 9/1996 | Acker et al. | |
| 5,725,578 A * | 3/1998 | Knapp et al. | 128/898 |
| 5,833,608 A | 11/1998 | Acker | |
| 5,913,820 A | 6/1999 | Bladen et al. | |
| 6,073,043 A * | 6/2000 | Schneider | 600/424 |
| 6,172,499 B1 | 1/2001 | Ashe | |
| 6,198,963 B1 | 3/2001 | Haim et al. | |
| 6,239,724 B1 | 5/2001 | Doron | |
| 6,301,545 B1 * | 10/2001 | Brodie | 701/213 |
| 6,396,438 B1 * | 5/2002 | Seal | 342/127 |
| 6,447,448 B1 * | 9/2002 | Ishikawa et al. | 600/300 |

(Continued)

FOREIGN PATENT DOCUMENTS

EP    0894473 A2    2/1999

(Continued)

OTHER PUBLICATIONS

European Search Report EP 02 25 8820 dated Oct. 14, 2003.

*Primary Examiner*—Brian Casler
*Assistant Examiner*—Baisakhi Roy
(74) *Attorney, Agent, or Firm*—Louis J Capezzuto

(57) ABSTRACT

Apparatus for tracking an object includes a plurality of field generators, which generate electromagnetic fields at different, respective frequencies in a vicinity of the object, and a radio frequency (RF) driver, which radiates a RF driving field toward the object. A wireless transponder is fixed to the object. The transponder includes at least one sensor coil, in which a signal current flows responsive to the electromagnetic fields, and a power coil, which receives the RF driving field and conveys electrical energy from the driving field to power the transponder. The power coil also transmits an output signal responsive to the signal current to a signal receiver, which processes the signal to determine coordinates of the object.

21 Claims, 3 Drawing Sheets

U.S. PATENT DOCUMENTS

2002/0154029 A1* 10/2002 Watters et al. ......... 340/870.07
2003/0167000 A1* 9/2003 Mullick et al. .............. 600/424

FOREIGN PATENT DOCUMENTS

| | | |
|---|---|---|
| EP | 0993804 A1 | 4/2000 |
| EP | 1321097 | 12/2002 |
| EP | 1136033 | 11/2004 |
| JP | 62032304 | 12/1987 |
| JP | 07500979 | 8/1992 |
| JP | 2001309892 | 11/2001 |
| WO | WO 93/04628 | 3/1993 |
| WO | WO 96/05768 A1 | 2/1996 |

* cited by examiner

WIRELESS POSITION SENSOR

FIELD OF THE INVENTION

The present invention relates generally to intrabody tracking systems, and specifically to wireless methods and devices for tracking the position and orientation of an object in the body.

BACKGROUND OF THE INVENTION

Many surgical, diagnostic, therapeutic and prophylactic medical procedures require the placement of objects such as sensors, treatment units, tubes, catheters, implants and other devices within the body. These procedures cover a large spectrum including, for example:
- insertion of electrodes for therapeutic or diagnostic purposes,
- placement of tubes to facilitate the infusion of drugs, nutritional and other fluids into a patient's circulatory system or digestive system,
- insertion of probes or surgical devices to facilitate cardiac or other types of surgery, and
- biopsies or other diagnostic procedures.

In many instances, insertion of a device is for a limited time, such as during surgery or catheterization. In other cases, devices such as feeding tubes or orthopedic implants are inserted for long-term use. The need exists for providing real-time information for accurately determining the location and orientation of objects within the patient's body, preferably without using X-ray imaging.

U.S. Pat. Nos. 5,391,199 and 5,443,489 to Ben-Haim, whose disclosures are incorporated herein by reference, describe systems wherein the coordinates of an intrabody probe are determined using one or more field sensors, such as a Hall effect device, coils, or other antennae carried on the probe. Such systems are used for generating three-dimensional location information regarding a medical probe or catheter. Preferably, a sensor coil is placed in the catheter and generates signals in response to externally-applied magnetic fields. The magnetic fields are generated by three radiator coils, fixed to an external reference frame in known, mutually spaced locations. The amplitudes of the signals generated in response to each of the radiator coil fields are detected and used to compute the location of the sensor coil. Each radiator coil is preferably driven by driver circuitry to generate a field at a known frequency, distinct from that of other radiator coils, so that the signals generated by the sensor coil may be separated by frequency into components corresponding to the different radiator coils.

U.S. Pat. No. 6,198,963 to Ben-Haim et al., whose disclosure is incorporated herein by reference, describes simplified apparatus for confirmation of intrabody tube location that can be operated by nonprofessionals. The initial location of the object is determined as a reference point, and subsequent measurements are made to determine whether the object has remained in its initial position. Measurements are based upon one or more signals transmitted to and/or from a sensor fixed to the body of the object whose location is being determined. The signal could be ultrasound waves, ultraviolet waves, radio frequency (RF) waves, or static or rotating electromagnetic fields.

PCT Patent Publication WO 96/05768 to Ben-Haim et al., whose disclosure is incorporated herein by reference, describes a system that generates six-dimensional position and orientation information regarding the tip of a catheter. This system uses a plurality of sensor coils adjacent to a locatable site in the catheter, for example near its distal end, and a plurality of radiator coils fixed in an external reference frame. These coils generate signals in response to magnetic fields generated by the radiator coils, which signals allow for the computation of six location and orientation coordinates.

U.S. Pat. No. 6,239,724 to Doron et al., whose disclosure is incorporated herein by reference, describes a telemetry system for providing spatial positioning information from within a patient's body. The system includes an implantable telemetry unit having (a) a first transducer, for converting a power signal received from outside the body into electrical power for powering the telemetry unit; (b) a second transducer, for receiving a positioning field signal that is received from outside the body; and (c) a third transducer, for transmitting a locating signal to a site outside the body, in response to the positioning field signal.

U.S. Pat. No. 6,172,499 to Ashe, whose disclosure is incorporated herein by reference, describes a device for measuring the location and orientation in the six degrees of freedom of a receiving antenna with respect to a transmitting antenna utilizing multiple-frequency AC magnetic signals. The transmitting component consists of two or more transmitting antennae of known location and orientation relative to one another. The transmitting antennae are driven simultaneously by AC excitation, with each antenna occupying one or more unique positions in the frequency spectrum. The receiving antennae measure the transmitted AC magnetic field plus distortions caused by conductive metals. A computer then extracts the distortion component and removes it from the received signals, providing the correct position and orientation output.

U.S. Pat. No. 4,173,228 to Van Steenwyck et al., whose disclosure is incorporated herein by reference, describes a catheter locating device based upon inducing a signal in a coil attached to the catheter and monitoring the amplitude and phase of the induced signal.

U.S. Pat. No. 5,099,845 to Besz et al., and U.S. Pat. No. 5,325,873 to Hirschi et al., whose disclosures are incorporated herein by reference, describe apparatus and methods in which a radiating element is fixed to a medical tube, e.g., a catheter, and the position of the tube is determined responsive to energy radiated from the element.

U.S. Pat. No. 5,425,382 to Golden, et al., whose disclosure is incorporated herein by reference, describes apparatus and methods for locating a medical tube in the body of a patient by sensing the static magnetic field strength gradient generated by a magnet fixed to the medical tube.

U.S. Pat. No. 4,905,698 to Strohl et al. and U.S. Pat. No. 5,425,367 to Shapiro, et al., whose disclosures are incorporated herein by reference, describe apparatus and methods wherein an applied magnetic field induces currents within a coil at the tip of a catheter. Based on these currents, the relative location of the catheter is determined.

U.S. Pat. No. 5,558,091 to Acker et al., whose disclosure is incorporated herein by reference, describes a magnetic position and orientation determining system which uses uniform fields from Helmholtz coils positioned on opposite sides of a sensing volume and gradient fields generated by the same coils. By monitoring field components detected at a probe during application of these fields, the position and orientation of the probe is deduced. A representation of the probe is superposed on a separately-acquired image of the subject to show the position and orientation of the probe with respect to the subject.

U.S. Pat. No. 5,913,820 to Bladen et al., whose disclosure is incorporated herein by reference, describes apparatus for locating the position of a sensor, preferably in three dimensions, by generating magnetic fields which are detected at the sensor. The magnetic fields are generated from a plurality of locations and enable both the orientation and location of a single coil sensor to be determined.

Commercial electrophysiological and physical mapping systems based on detecting the position of a probe inside the body are presently available. Among them, CARTO™, developed and marketed by Biosense Webster Inc., Diamond Bar, Calif., is a system for automatic association and mapping of local electrical activity with catheter location.

An article entitled, "Microtool Opens 3D Window into the Human Body," by Cleopatra Alfenito, *Medical Imaging* 12(11) (November, 1997), which is incorporated herein by reference, describes the "miniBIRD" device, made by Ascension Technology (Burlington, Vt.). This device "... measures internal organs and their motion by reconstructing the position and orientation of 2D slices to fill a 3D volume ... Sensors—as small as 5 mm—can be attached to probes, instruments, or even a fetal head inside the human body. These mini-trackers measure the spatial location of ultrasound probes or other instruments with six degrees of freedom (position and orientation as given by x,y,z, yaw, pitch and roll) in real time. The miniBIRD works by measuring magnetic fields and converting signals to real-time 3D measurements. At the start of each measurement cycle (of which there are up to 144 per second), the system's triaxial transmitter is driven by a pulsed DC signal. The sensor then measures the transmitted magnetic field pulse. The electronics unit controls the transmitting and receiving elements and converts the received signals into real-time position and orientation measurements, providing for the collection of accurate data. This data can then be used for 3D reconstruction of internal images of the heart, blood vessels, stomach, pelvis and other areas as provided by ultrasound or an endoscope."

SUMMARY OF THE INVENTION

It is an object of some aspects of the present invention to provide improved apparatus and methods for real-time determination of the location and orientation of intrabody objects.

It is a further object of some aspects of the present invention to provide improved position measurement apparatus and methods based on radio frequency signals.

It is yet a further object of some aspects of the present invention to provide improved apparatus and methods for determining intrabody object location and orientation which can operate in the absence of other locating technologies such as MRI or fluoroscopy.

It is still a further object of some aspects of the present invention to provide a sensor for intrabody object location that requires neither wiring nor an internal power source.

It is an additional object of some aspects of the present invention to provide apparatus for intrabody mapping that is light in weight and small in size.

It is yet an additional object of some aspects of the present invention to provide intrabody mapping apparatus which can readily be integrated into existing mapping support systems.

In preferred embodiments of the present invention, apparatus for sensing the position and orientation of an object placed within a patient's body comprises a wireless location transponder containing a power coil, a sensing coil, and a signal processing chip. Typically, the transponder is fixed to a device inserted into the body, such as a catheter or implant. An externally-located driving unit sends a radio frequency (RF) signal, preferably having a frequency in the megahertz range, to drive the power coil in the transponder and thereby power the chip. Additionally, a set of magnetic field generators in fixed locations outside the body produce magnetic fields at different, respective frequencies, typically in the kilohertz range. These fields cause currents to flow in the sensing coil, which depend on the spatial position and orientation of the sensing coil relative to the field generators. The processing chip converts these currents into high-frequency signals, which are transmitted by the power coil to an externally-located signal processing unit. This unit processes the signal in order to determine position and orientation coordinates of the object for display and recording.

Thus, in contrast to current medical tracking systems, such as the above-mentioned CARTO™ system, the present transponder enables the position and orientation of an object in the body to be determined without the need for any wired connection between the sensing coil and the external processing unit. This sort of wireless operation is particularly advantageous for visualizing the position of implantable devices, which cannot readily be wired to the processing unit. It is also useful in reducing the number of wires that must be passed through an invasive probe, such as a catheter, in order to operate a position sensor at its distal end. By reducing the number of wires, it is typically possible to reduce the diameter of the probe. Furthermore, because the present transponder uses only two coils, with a single coil serving for both power input and signal output, and no internal power source, it can be made substantially smaller than wireless transponders known in the art.

Preferably, a clock synchronizer is used to synchronize the signals produced by both the external driving unit and the magnetic field generators. Most preferably, the frequency of the RF driving signal is set to be an integer multiple of the magnetic field frequencies. This clock synchronization enables the transponder chip to use phase-sensitive detection in order to enhance the signal/noise ratio of the signal from the sensor coil. The phase of the sensor signals is preferably also used to resolve ambiguity that would otherwise occur in the signals under 180° reversal of the sensor coil axis.

Alternatively or additionally, the transponder may comprise multiple sensor coils, preferably three mutually-orthogonal coils, as described in the above-mentioned PCT publication WO 96/05768. In this case, all six position and orientation coordinates can be determined without ambiguity.

A further advantage of some preferred embodiments of the present invention is that they can be readily integrated into existing electromagnetic catheter-tracking systems, such as the above-mentioned CARTO™ mapping system. In such embodiments, the driving unit and an accompanying receiver, for communicating over the air with the power coil of the wireless transponder, are connected to the processing unit of the tracking system in place of the wires that normally convey position signals from the catheter. The receiver preprocesses the signals that it receives from the power coil, and then passes the signals on to the existing signal processor in the tracking system for position determination and display.

There is therefore provided, in accordance with a preferred embodiment of the present invention, apparatus for tracking an object, including:

a plurality of field generators, adapted to generate electromagnetic fields at different, respective frequencies in a vicinity of the object;

a radio frequency (RF) driver, adapted to radiate a RF driving field toward the object;

a wireless transponder, fixed to the object, the transponder including:

at least one sensor coil, coupled so that an electrical current flows in the at least one sensor coil responsive to the electromagnetic fields;

a control circuit, coupled to the at least one sensor coil so as to generate an output signal indicative of the current; and a power coil, coupled to receive the RF driving field and to convey electrical energy from the driving field to the control circuit, and further coupled to transmit the output signal generated by the control circuit; and a signal receiver, adapted to receive the output signal transmitted by the power coil and, responsive thereto, to determine coordinates of the object.

Preferably, the electrical current in the at least one sensor coil has frequency components at the different frequencies of the one or more field generators, and the signal generated by the control circuit is indicative of the frequency components of the current.

Additionally or alternatively, the one or more field generators are adapted to generate the electromagnetic fields at respective field frequencies, and the RF driver is adapted to radiate the RF driving field at a driving frequency, and the one or more field generators and the RF driver are coupled to operate so that the field frequencies and driving frequency are mutually synchronized.

Further additionally or alternatively, the control circuit is adapted to generate the output signal so as to indicate a phase of the current flowing in the at least one sensor coil, relative to a phase of the electromagnetic fields.

In a preferred embodiment, the control circuit includes a voltage-to-frequency (V/F) converter, which is coupled to generate the output signal with an output frequency that varies responsive to the electrical current flowing in the at least one sensor coil.

In some preferred embodiments, the transponder is adapted to be inserted, together with the object, into a body of a subject, while the one or more field generators and the RF driver are placed outside the body. Preferably, the object includes an elongate probe, for insertion into the body, and the transponder is fixed in the probe so as to enable the receiver to determine the coordinates of a distal end of the probe. Alternatively, the object includes an implant, and the transponder is fixed in the implant so as to enable the receiver to determine the coordinates of the implant within the body. In a preferred embodiment, the implant include a hip joint implant, including a femur head and an acetabulum, and the transponder includes a plurality of transponders fixed respectively to the femur head and the acetabulum, and the signal receiver is adapted to determine a distance between the femur head and the acetabulum responsive to the output signal from the transponders.

Preferably, the control circuit is adapted to operate powered solely by the electrical energy conveyed thereto by the power coil.

There is also provided, in accordance with a preferred embodiment of the present invention, apparatus for tracking an object, including:

a radio frequency (RF) driver, adapted to radiate a RF driving field toward the object at a driving frequency;

one or more field generators, adapted to generate electromagnetic fields in a vicinity of the object at respective field frequencies, in synchronization with the driving frequency;

a wireless transponder, fixed to the object, the transponder including:

at least one sensor coil, coupled so that an electrical current flows in the at least one sensor coil responsive to the electromagnetic fields;

a control circuit, coupled to the at least one sensor coil so as to generate an output signal indicative of the current; and a power coil, coupled to receive the RF driving field and to convey electrical energy from the driving field to the control circuit, and further coupled to transmit the output signal generated by the control circuit; and a signal receiver, adapted to receive the output signal transmitted by the power coil and, responsive thereto, to determine coordinates of the object.

There is additionally provided, in accordance with a preferred embodiment of the present invention, apparatus for tracking an object, including:

a radio frequency (RF) driver, adapted to radiate a RF driving field toward the object;

one or more field generators, adapted to generate electromagnetic fields in a vicinity of the object;

a wireless transponder, fixed to the object, the transponder including:

at least one sensor coil, coupled so that an electrical current flows in the at least one sensor coil responsive to the electromagnetic fields;

a control circuit, coupled to the at least one sensor coil so as to generate an output signal indicative of an amplitude of the current and of a phase of the current relative to a phase of the electromagnetic fields; and a power coil, coupled to receive the RF driving field and to convey electrical energy from the driving field to the control circuit, and further coupled to transmit the output signal generated by the control circuit; and a signal receiver, adapted to receive the output signal transmitted by the power coil and, responsive to the amplitude and phase of the current indicated by the output signal, to determine an orientation of the object.

In a preferred embodiment, the at least one sensor coil includes a single sensor coil, and the signal receiver is adapted, responsive to the indicated phase of the current, to determine a direction of the orientation of the transponder.

There is further provided, in accordance with a preferred embodiment of the present invention, apparatus for tracking an object, including:

a radio frequency (RF) driver, adapted to radiate a RF driving field toward the object;

one or more field generators, adapted to generate electromagnetic fields in a vicinity of the object;

a wireless transponder, fixed to the object, the transponder including:

at least one sensor coil, coupled so that an electrical current flows in the at least one sensor coil responsive to the electromagnetic fields;

a voltage-to-frequency (V/F) converter, coupled to the at least one sensor coil so as to generate an output signal with an output frequency that varies responsive to an amplitude of the electrical current flowing in the at least one sensor coil; and a power coil, coupled to receive the RF driving field and to convey electrical energy from the driving field to the control circuit, and further coupled to transmit the output signal generated by the control circuit; and a signal receiver, adapted to receive the output signal transmitted by the power coil and, responsive to the output frequency, to determine coordinates of the object.

There is moreover provided, in accordance with a preferred embodiment of the present invention, a wireless position transponder for operation inside a body of a subject, the transponder including:

at least one sensor coil, coupled so that an electrical current flows in the at least one sensor coil responsive to one or more electromagnetic fields applied to the body in a vicinity of the transponder;

a voltage-to-frequency (V/F) converter, coupled to the at least one sensor coil so as to generate an output signal with an output frequency that varies responsive to an amplitude of the electrical current flowing in the at least one sensor coil, such that the output frequency is indicative of coordinates of the transponder inside the body; and a power coil, adapted to receive a radio frequency (RF) driving field applied to the body in the vicinity of the transponder, and coupled to convey electrical energy from the driving field to the control circuit, and further coupled to transmit the output signal generated by the control circuit so that the signal can be received by processing circuitry outside the body for use in determining the coordinates.

In a preferred embodiment, the sensor coil, V/F converter and power coil are together adapted to be fixed inside an elongate probe, for insertion into the body, so as to enable the processing circuitry to determine the coordinates of a distal end of the probe.

In another preferred embodiment, the sensor coil, V/F converter and power coil are together adapted to be fixed inside an implant, so as to enable the processing circuitry to determine the coordinates of the implant within the body.

Preferably, the V/F converter is adapted to operate powered solely by the electrical energy conveyed thereto by the power coil.

There is furthermore provided, in accordance with a preferred embodiment of the present invention, a method for tracking an object, including:

positioning a plurality of field generators so as to generate electromagnetic fields at different, respective frequencies in a vicinity of the object;

positioning a radio frequency (RF) driver to radiate a RF driving field toward the object;

fixing to the object a wireless transponder including at least one sensor coil and a power coil, so that an electrical current flows in the at least one sensor coil responsive to the electromagnetic fields;

receiving the RF driving field using the power coil so as to derive electrical energy therefrom;

generating an output signal at the wireless transponder indicative of the current flowing in the sensor coil, using the electrical energy derived from the RF driving field by the power coil;

transmitting the output signal from the wireless transponder using the power coil; and receiving and processing the output signal to determine coordinates of the object.

In a preferred embodiment, generating the output signal includes generating the signal with an output frequency that varies responsive to an amplitude of the electrical current flowing in the at least one sensor coil.

In some preferred embodiments, the method includes inserting the transponder, together with the object, into a body of a subject, wherein positioning the plurality of the field generators and the RF driver includes placing the one or more field generators and the RF driver outside the body. In one of these embodiments, the object includes an implant, and fixing the transponder to the object includes fixing the transponder to the implant, and receiving and processing the output signal includes determining the coordinates of the implant within the body. Typically, the implant includes a hip joint implant, including a femur head and an acetabulum, and fixing the transponder includes fixing a plurality of transponders respectively to the femur head and the acetabulum, and determining the coordinates of the implant includes determining a distance between the femur head and the acetabulum responsive to the output signal from the transponders. Preferably, determining the distance includes finding the distance using the transponders during both intraoperative and post-operative periods.

There is also provided, in accordance with a preferred embodiment of the present invention, a method for tracking an object, including:

positioning a radio frequency (RF) driver to radiate a RF driving field toward the object at a driving frequency;

positioning one or more field generators so as to generate electromagnetic fields in a vicinity of the object at respective field frequencies, in synchronization with the driving frequency;

fixing to the object a wireless transponder including at least one sensor coil and a power coil, so that an electrical current flows in the at least one sensor coil responsive to the electromagnetic fields;

receiving the RF driving field using the power coil so as to derive electrical energy therefrom;

generating an output signal at the wireless transponder indicative of the current flowing in the sensor coil, using the electrical energy derived from the RF driving field by the power coil;

transmitting the output signal from the wireless transponder using the power coil; and receiving and processing the output signal to determine coordinates of the object.

There is additionally provided, in accordance with a preferred embodiment of the present invention, a method for tracking an object, including:

positioning a radio frequency (RF) driver to radiate a RF driving field toward the object;

positioning one or more field generators so as to generate electromagnetic fields in a vicinity of the object;

fixing to the object a wireless transponder including at least one sensor coil and a power coil, so that an electrical current flows in the at least one sensor coil responsive to the electromagnetic fields;

receiving the RF driving field using the power coil so as to derive electrical energy therefrom;

generating an output signal at the wireless transponder indicative of an amplitude of the current flowing in the at least one sensor coil and of a phase of the current relative to a phase of the electromagnetic fields, using the electrical energy derived from the RF driving field by the power coil;

transmitting the output signal from the wireless transponder using the power coil; and receiving the output signal, and processing the amplitude and phase of the current indicated by the output signal to determine an orientation of the object.

There is further provided, in accordance with a preferred embodiment of the present invention, a method for tracking an object, including:

positioning a radio frequency (RF) driver to radiate a RF driving field toward the object;

positioning one or more field generators so as to generate electromagnetic fields in a vicinity of the object;

fixing to the object a wireless transponder including at least one sensor coil and a power coil, so that an electrical current flows in the at least one sensor coil responsive to the electromagnetic fields;

receiving the RF driving field using the power coil so as to derive electrical energy therefrom;

generating an output signal at the wireless transponder having an output frequency that varies responsive to an amplitude of the current flowing in the at least one sensor coil, using the electrical energy derived from the RF driving field by the power coil;

transmitting the output signal from the wireless transponder using the power coil; and receiving and processing the output signal to determine coordinates of the object, responsive to the output frequency.

The present invention will be more fully understood from the following detailed description of the preferred embodiments thereof, taken together with the drawings, in which:

DETAILED DESCRIPTION OF PREFERRED EMBODIMENTS

Figure 1:
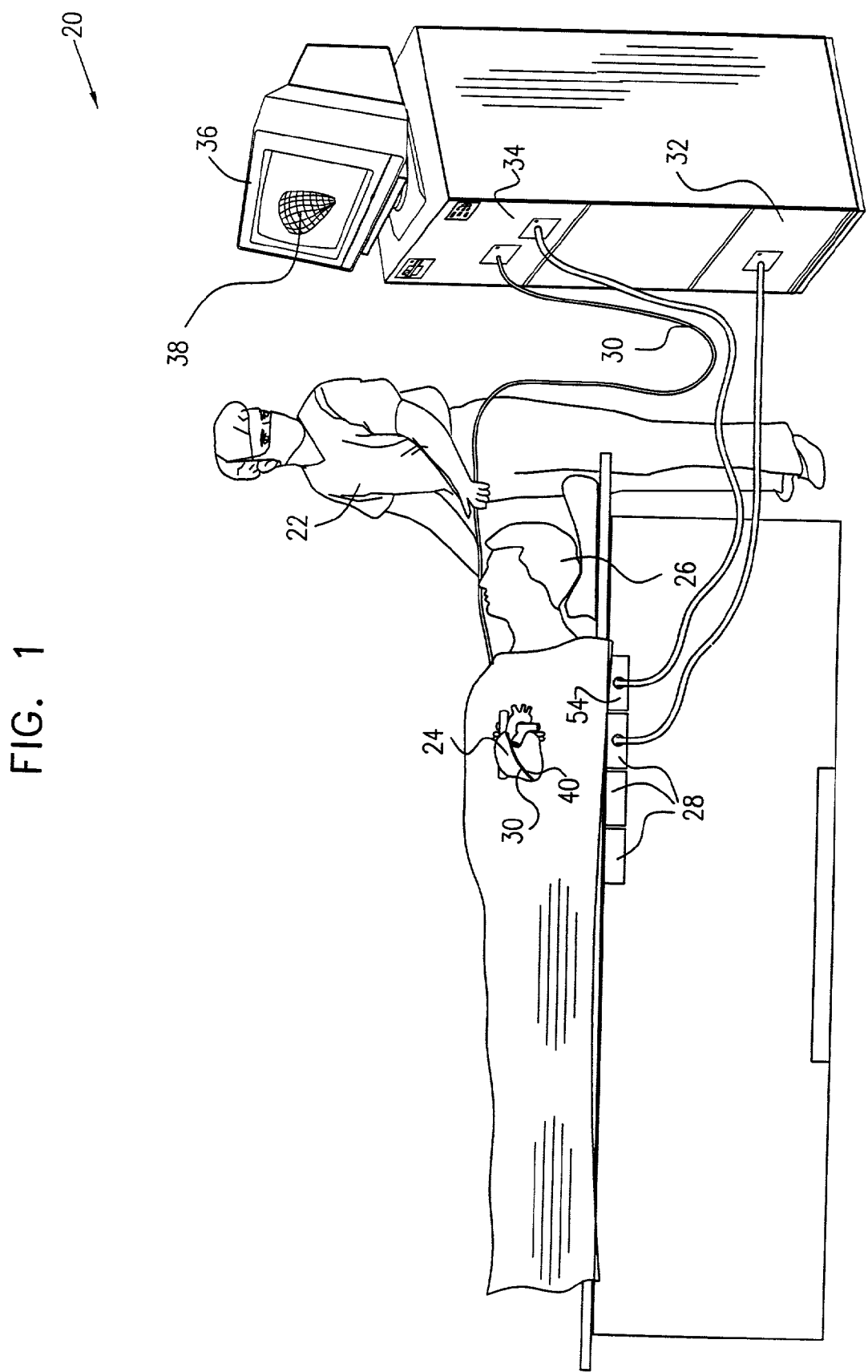
FIG. 1 is a schematic, pictorial illustration of a system for tracking the position of a catheter in the heart, in accordance with a preferred embodiment of the present invention.

FIG. 1 is a schematic, pictorial illustration of a mapping system 20, for mapping a heart 24 of a subject 26, in accordance with a preferred embodiment of the present invention. System 20 comprises an elongate probe, preferably a catheter 30, which is inserted by a user 22 through a vein or artery of the subject into a chamber of the heart. Catheter 30 comprises a wireless position transponder 40, preferably near the distal tip of the catheter. Transponder 40 is shown in detail in FIG. 2. Optionally, catheter 30 comprises two or more transponders of this sort, mutually spaced along the length of the catheter, in order to give position and orientation coordinates at multiple points along the catheter.

To operate transponder 40, subject 26 is placed in a magnetic field generated, for example, by situating under the subject a pad containing field generator coils 28 for generating a magnetic field. Coils 28 are driven by driver circuits 32 to generate electromagnetic fields at different, respective frequencies. The generator coils 28 are located external to the subject (patient) 26. A reference electromagnetic sensor (not shown) is preferably fixed relative to the patient, for example, taped to the patient's back, and catheter 30 containing transponder 40 is advanced into the patient's heart. An additional antenna 54, preferably in the form of a coil, provides RF power to the transponder and receives signals therefrom, as described in detail hereinbelow. Signals received by antenna 54 from transponder 40 in the heart are conveyed to a console 34, which analyzes the signals and then displays the results on a monitor 36. By this method, the precise location of transponder 40 in catheter 30, relative to the reference sensor, can be ascertained and visually displayed. The transponder can also detect displacement of the catheter that is caused by contraction of the heart muscle.

Some of the features of system 20 are implemented in the above-mentioned CARTO™ system, including the use of the system to generate maps 38 of cardiac electrical and mechanical function. Further aspects of the design of catheter 30 and of system 20 generally are described in the above-mentioned U.S. Pat. Nos. 5,391,199, 5,443,489 and 6,198,963. The design of transponder 40 and the associated driver and signal processing circuits used in console 34, however, as described hereinbelow, are unique to the present invention.

Figure 2:
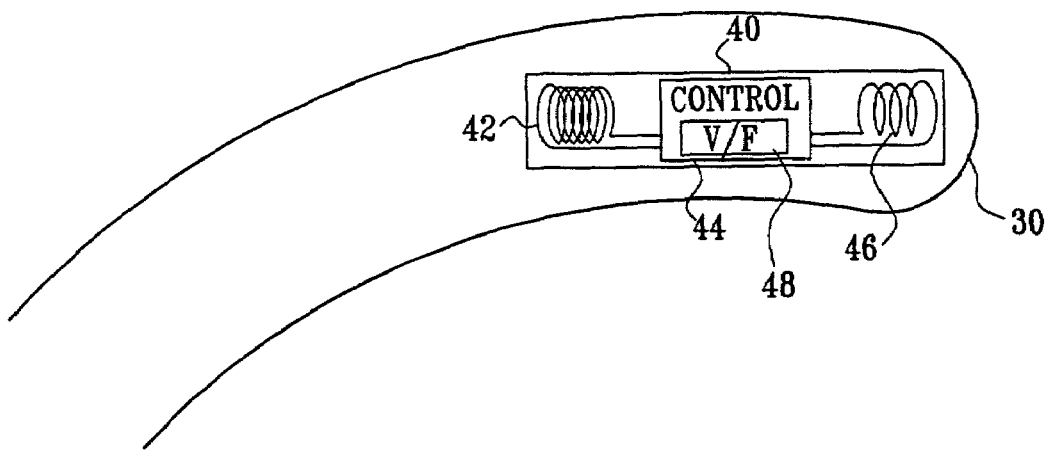
FIG. 2 is a schematic side view of a catheter, showing details of a wireless location transponder in the catheter, in accordance with a preferred embodiment of the present invention.
Figure 3:
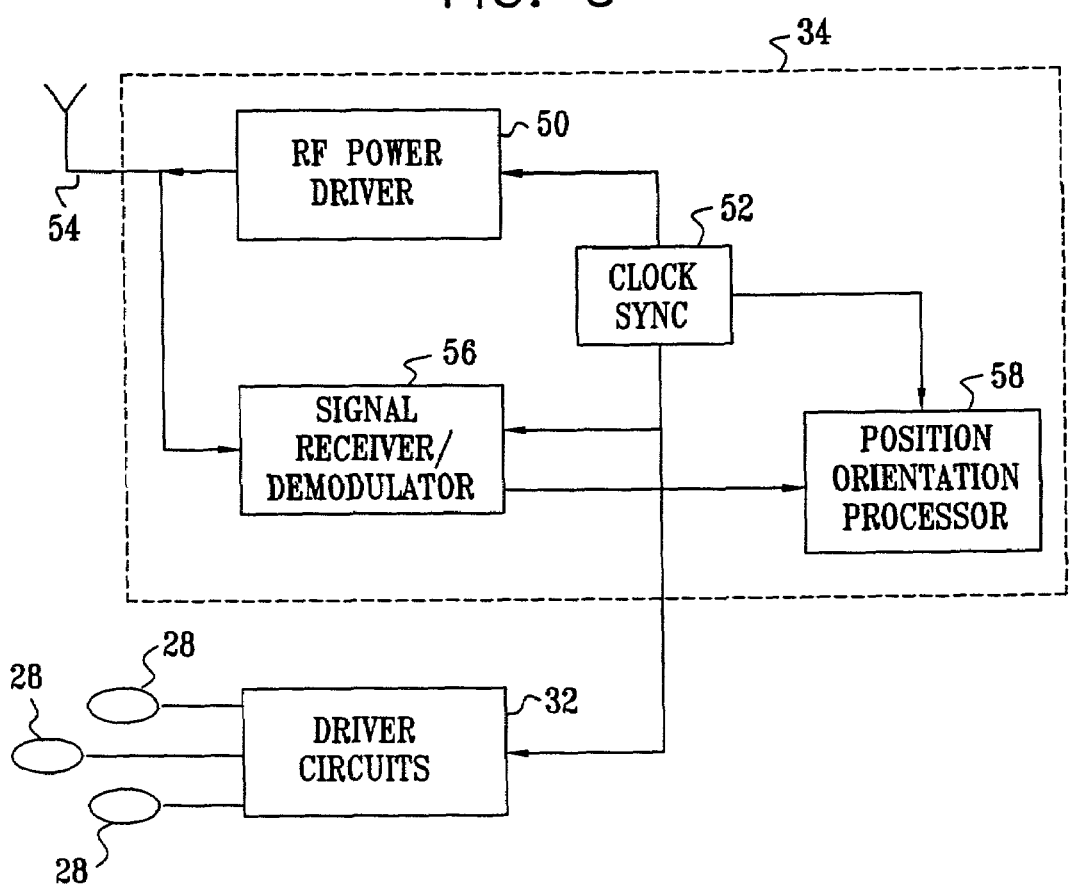
FIG. 3 is a block diagram that schematically illustrates elements of driver and processing circuitry used in a wireless position sensing system, in accordance with a preferred embodiment of the present invention.

Reference is now made to FIGS. 2 and 3, which schematically show details of transponder 40 and of driving and processing circuits in console 34, in accordance with a preferred embodiment of the present invention. As shown in FIG. 2, transponder 40 comprises a power coil 42 and a sensing coil 46, coupled to a control chip 44. Coil 42 is preferably optimized to receive and transmit high-frequency signals, in the range above 1 MHz. Coil 46, on the other hand, is preferably designed for operation in the range of 1-3 kHz, the frequencies at which coils 28 generate their electromagnetic fields. Alternatively, other frequency ranges may be used, as dictated by application requirements. The entire transponder 40 is typically 2-5 mm in length and 2-3 mm in outer diameter, enabling it to fit conveniently inside catheter 30.

As shown in FIG. 3, console 34 comprises a RF power driver 50, which drives antenna 54 to emit a power signal, preferably in the 2-10 MHz range. The power signal causes a current to flow in power coil 42, which is rectified by chip 44 and used to power its internal circuits. Meanwhile, the electromagnetic fields produced by field generator coils 28 cause a current to flow in sensor coil 46. This current has frequency components at the same frequencies as the driving currents flowing through the generator coils. The current components are proportional to the strengths of the components of the respective magnetic fields produced by the generator coils in a direction parallel to the sensor coil axis. Thus, the amplitudes of the currents indicate the position and orientation of coil 46 relative to fixed generator coils 28.

Chip 44 measures the currents flowing in sensor coil 46 at the different field frequencies. It encodes this measurement in a high-frequency signal, which it then transmits back via power coil 42 to antenna 54. Preferably, chip 44 comprises a voltage-to-frequency (V/F) converter 48, which generates a RF signal whose frequency is proportional to the voltage produced by the sensor coil current flowing across a load. Preferably, the RF signal produced by chip 44 has a carrier frequency in the 50-150 MHz range. The RF signal produced in this manner is modulated with three different frequency modulation (FM) components that vary over time at the respective frequencies of the fields generated by coils 28. The magnitude of the modulation is proportional to the current components at the three frequencies. An advantage of using frequency modulation, rather than amplitude modulation, to convey the sensor coil amplitude measurements from transponder 40 to antenna 54 is that the information in the signal (i.e., the frequency) is unaffected by the variable attenuation of the body tissues through which the signal must pass.

Alternatively, chip 44 may comprise a sampling circuit and analog/digital (A/D) converter (not shown in the figures), which digitizes the amplitude of the current flowing in sensor coil 46. In this case, chip 44 generates an digitally-modulated signal, and RF-modulates the signal for transmission by power coil 42. Any suitable method of digital encoding and modulation may be used for this purpose. Other methods of signal processing and modulation will be apparent to those skilled in the art.

The FM or digitally-modulated signal transmitted by power coil 42 is picked up by a receiver 56, coupled to antenna 54. The receiver demodulates the signal to generate a suitable input to signal processing circuits 58 in console 34. Typically, receiver 56 amplifies, filters and digitizes the signals from transponder 40. The digitized signals are received and used by processing circuits 58 to compute the position and orientation of catheter 30. Typically, circuits 58 comprise a general-purpose computer, which is programmed and equipped with appropriate input circuitry for processing the signals from receiver 56. The information derived by circuits 58 is used to generate map 38, for example, or to provide other diagnostic information or guidance to operator 22.

In an alternative embodiment of the present invention, driver 50, receiver 56 and antenna 54 are retrofitted to an existing tracking system, such as a CARTO™ system. Console 34 in the existing system is designed to receive and process signals received over wires from one or more sensor coils in catheter 30, using existing processing circuits 58 to determine the position and orientation of the catheter. Therefore, in this alternative embodiment, receiver 56 demodulates the signals generated by transponder 40 so as to reconstruct the variable current signals generated by sensor coil 46. The existing processing circuits use this information to determine the catheter position and orientation just as if the sensor coil currents had been received by wired connection.

Preferably, console 34 includes a clock synchronization circuit 52, which is used to synchronize driver circuits 32 and RF power driver 50. Most preferably, the RF power driver operates at a frequency that is an integer multiple of the driving frequencies of field generators 28. Chip 44 can then use the RF signal received by power coil 42 not only as its power source, but also as a frequency reference. Using this reference, chip 44 is able to apply phase-sensitive processing to the current signals generated by sensor coil 46, to detect the sensor coil current in phase with the driving fields generated by coils 28. Receiver 56 can apply phase-sensitive processing methods, as are known in the art, in a similar manner, using the input from clock synchronization circuit 52. Such phase-sensitive detection methods enable transponder 40 to achieve an enhanced signal/noise (S/N) ratio, despite the low amplitude of the current signals in sensor coil 46.

The single sensor coil 46 shown in FIG. 2 is sufficient, in conjunction with field generator coils 28, to enable processing circuits 58 to generate three dimensions of position and two dimensions of orientation information. The third dimension of orientation (typically rotation of catheter 30 about its longitudinal axis) can be inferred if needed from mechanical information or, when two or more transponders are used in the catheter, from a comparison of their respective coordinates. Alternatively, transponder 40 may comprise multiple sensor coils, preferably three mutually-orthogonal coils, as described, for example, in the above-mentioned PCT publication WO 96/05768. In this case, processing circuits can determine all six position and orientation coordinates of catheter 30 unambiguously.

Another point of possible ambiguity in determining the orientation coordinates of transponder 40 is that the magnitude of the currents flowing in sensor coil 46 is invariant under reversal of the direction of the axis of the coil. In other words, flipping transponder 40 by 180° through a plane perpendicular to the axis of the sensor coil has no effect on the current amplitude. Under some circumstances, this symmetrical response could cause an error of 180° in determining the coordinates of the transponder.

While the magnitude of the sensor coil current is unaffected by flipping the coil axis, the 180° reversal does reverse the phase of the current relative to the phase of the driving electromagnetic fields generated by field generators 28. Clock synchronization circuit 52 can be used to detect this phase reversal and thus overcome the ambiguity of orientation under 180° rotation. Synchronizing the modulation of the RF signal returned by chip 44 to receiver 56 with the currents driving field generators 28 enables receiver 56 to determine the phase of the currents in sensor coil 46 relative to the driving currents. By checking whether the sensor currents are in phase with the driving currents or 180° out of phase, processing circuitry 58 is able to decide in which direction the transponder is pointing.

Figure 4:
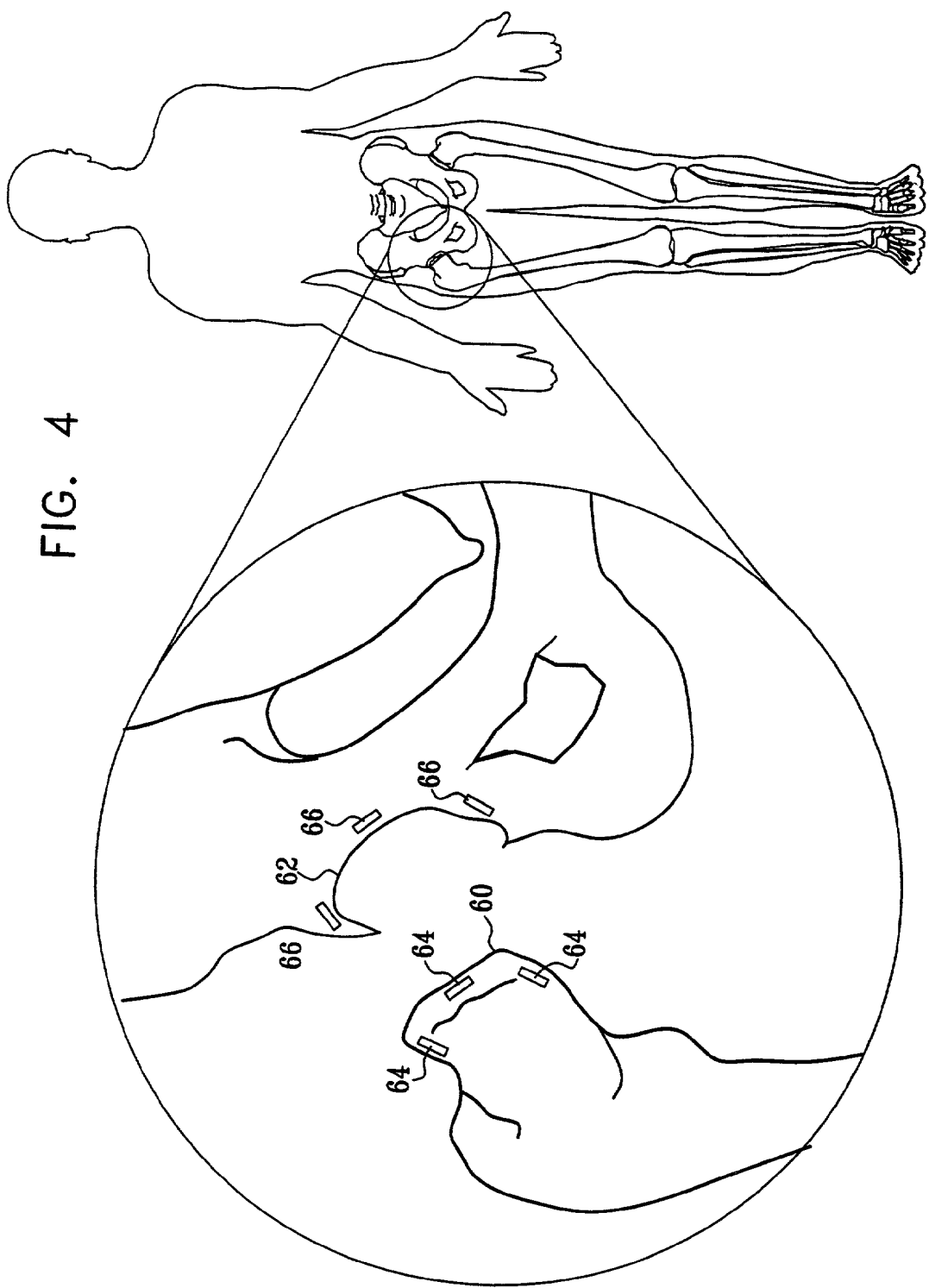
FIG. 4 is a schematic, pictorial illustration showing the use of wireless location transponders in a joint implant, in accordance with a preferred embodiment of the present invention.

FIG. 4 is a schematic, pictorial illustration showing the use of location transponders in an orthopedic procedure, in accordance with a preferred embodiment of the present invention. An advantage of using wireless transponders, such as transponder 40, without an on-board power source, is that the transponders can be inserted in or attached to implantable devices, and then left inside the patient's body for later reference. The embodiment shown in FIG. 4 illustrates hip implant surgery, in which a surgeon is required to position the head of an artificial femur 60 in an artificial acetabulum 62. Typically, before performing the procedure, the surgeon takes X-rays or CT images to visualize the area of the operation, but then must perform the actual surgery without the benefit of real-time three-dimensional visualization.

In the embodiment shown in FIG. 4, miniature transponders 64 are embedded in femur 60, and further miniature transponders 66 are embedded in the pelvis in the area of acetabulum 62. Transponders 64 and 66 are preferably similar to transponder 40, as shown in FIG. 2. Most preferably, each transponder is configured to transmit signals back to antenna 54 at a different carrier frequency, so that receiver 56 can differentiate between the transponders. At the beginning of surgery, an X-ray image is taken with the head of the femur in proximity to the acetabulum. The image is captured by computer and displayed on a computer monitor. Transponders 64 and 66 are visible in the X-ray image, and their positions in the image are registered with their respective location coordinates, as determined by processing circuitry 58. During the surgery, the movement of the transponders is tracked by circuitry 58, and this movement is used to update the relative positions of the femur and acetabulum in the image on the monitor, using image processing techniques known in the art. The surgeon uses the updated image to achieve proper placement of the femur head in the acetabulum, without the need for repeated X-ray exposures while the surgery is in process.

After the surgery is finished, the relative positions of transponders 64 and 66 (which remain in the implant) are preferably checked periodically to verify that the proper relation is maintained between the bones. This sort of position monitoring is useful both during recovery and for monitoring the status of the implant over the long term. For example, such monitoring may be used to detect increasing separation of the femur from the acetabulum, which is known in some cases to precede more serious bone deterioration.

While FIGS. 1 and 4 show only two particular applications of wireless position transponders in accordance with preferred embodiments of the present invention, other applications will be apparent to those skilled in the art and are considered to be within the scope of the present invention. For example, and not by way of limitation, such transponders may be fixed to other types of invasive tools, such as endoscopes and feeding tubes, as well as to other implantable devices, such as orthopedic implants used in the knee, the spine and other locations.

It will thus be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for tracking an object in a body of a subject, comprising:
a plurality of field generators, adapted to generate electromagnetic fields at different, respective frequencies in a vicinity of the object;
a radio frequency (RF) driver, adapted to radiate a RF driving field toward the object;
a wireless transponder, adapted to be fixed to the object, the transponder comprising:
at least one sensor coil, coupled so that an electrical current flows in the at least one sensor coil responsive to the electromagnetic fields;
a control circuit, coupled to the at least one sensor coil so as to generate an output signal indicative of the current; and
a power coil, coupled to receive the RF driving field and to convey electrical energy from the driving field to the control circuit, and further coupled to transmit the output signal generated by the control circuit; and a signal receiver, adapted to receive the output signal transmitted by the power coil and, responsive thereto, and signal processing circuits operatively connected to the signal receiver for determining three dimensions of position information and at least two dimensions of orientation information wherein the information is the position and orientation coordinates of the object in the body of the subject.

2. Apparatus according to claim 1, wherein the electrical current in the at least one sensor coil has frequency components at the different frequencies of the one or more field generators, and wherein the signal generated by the control circuit is indicative of the frequency components of the current.

3. Apparatus according to claim 1, wherein the one or more field generators are adapted to generate the electromagnetic fields at respective field frequencies, and the RF driver is adapted to radiate the RF driving field at a driving frequency, and wherein the one or more field generators and the RF driver are coupled to operate so that the field frequencies and driving frequency are mutually synchronized.

4. Apparatus according to claim 1, wherein the control circuit is adapted to generate the output signal so as to indicate a phase of the current flowing in the at least one sensor coil, relative to a phase of the electromagnetic fields.

5. Apparatus according to claim 1, wherein the control circuit comprises a voltage-to-frequency (V/F) converter, which is coupled to generate the output signal with an output frequency that varies responsive to the electrical current flowing in the at least one sensor coil.

6. Apparatus according to claim 1, wherein the transponder is adapted to be inserted, together with the object, into a body of a subject, while the one or more field generators and the RF driver are placed outside the body.

7. Apparatus according to claim 6, wherein the object comprises an elongate probe, for insertion into the body, and wherein the transponder is fixed in the probe so as to enable the receiver to determine the coordinates of a distal end of the probe.

8. Apparatus according to claim 6, wherein the object comprises an implant, and wherein the transponder is fixed in the implant so as to enable the receiver to determine the coordinates of the implant within the body.

9. Apparatus according to claim 8, wherein the implant comprise a hip joint implant, comprising a femur head and an acetabulum, and wherein the transponder comprises a plurality of transponders fixed respectively to the femur head and the acetabulum, and wherein the signal receiver is adapted to determine a distance between the femur head and the acetabulum responsive to the output signal from the transponders.

10. Apparatus according to claim 1, wherein the control circuit is adapted to operate powered solely by the electrical energy conveyed thereto by the power coil.

11. A method for tracking an object in a body of a subject, comprising:
positioning a plurality of field generators so as to generate electromagnetic fields at different, respective frequencies in a vicinity of the object;
positioning a radio frequency (RF) driver to radiate a RF driving field toward the object;
adapting to be fixed to the object, a wireless transponder comprising at least one sensor coil and a power coil, so that an electrical current flows in the at least one sensor coil responsive to the electromagnetic fields;
receiving the RF driving field using the power coil so as to derive electrical energy therefrom;
generating an output signal at the wireless transponder indicative of the current flowing in the sensor coil,
using the electrical energy derived from the RF driving field by the power coil;
transmitting the output signal from the wireless transponder using the power coil; and
receiving and processing the output signal to determine three dimensions of position information and at least two dimensions of orientation information wherein the information is position and orientation coordinates of the object in the body of the subject.

12. A method according to claim 11, wherein the electrical current in the at least one sensor coil has frequency components at the different frequencies of the one or more field generators, and wherein generating the output signal comprises generating the output signal responsive to the frequency components of the current.

13. A method according to claim 11, wherein positioning the one or more field generators and the RF driver comprises synchronizing respective field frequencies of the one or more field generators with a driving frequency of the RF driver.

14. A method according to claim 11, wherein generating the output signal comprises producing the output signal so as to indicate a phase of the current flowing in the at least one sensor coil, relative to a phase of the electromagnetic fields.

15. A method according to claim 11, wherein generating the output signal comprises generating the signal with an output frequency that varies responsive to an amplitude of the electrical current flowing in the at least one sensor coil.

16. A method according to claim 11, and comprising inserting the transponder, together with the object, into a body of a subject, wherein positioning the plurality of the field generators and the RF driver comprises placing the one or more field generators and the RF driver outside the body.

17. A method according to claim 16, wherein the object comprises an elongate probe, for insertion into the body, and wherein fixing the transponder to the object comprises fixing the transponder in the probe, and wherein receiving and processing the output signal comprises determining the coordinates of a distal end of the probe in the body.

18. A method according to claim 16, wherein the object comprises an implant, and wherein fixing the transponder to the object comprises fixing the transponder to the implant, and wherein receiving and processing the output signal comprises determining the coordinates of the implant within the body.

19. A method according to claim 16, wherein the implant comprise a hip joint implant, comprising a femur head and an acetabulum, and wherein fixing the transponder comprises fixing a plurality of transponders respectively to the femur head and the acetabulum, and wherein determining the coordinates of the implant comprises determining a distance between the femur head and the acetabulum responsive to the output signal from the transponders.

20. A method according to claim 19, wherein determining the distance comprises finding the distance using the transponders during both intraoperative and post-operative periods.

21. A method according to claim 11, wherein generating the output signal comprises operating the transponder powered solely by the electrical energy derived from the RF driving field by the power coil.

* * * * *